United States Patent
Pyun et al.

(10) Patent No.: US 9,907,472 B2
(45) Date of Patent: Mar. 6, 2018

(54) DISEASE DIAGNOSIS AND SKIN AGE MEASUREMENT APPARATUS USING LASER IRRADIATION DEVICE AND DETACHABLE HANDPIECE USED IN THE SAME

(71) Applicant: Speclipse, Inc., Seoul (KR)

(72) Inventors: Sung Hyun Pyun, Seoul (KR); Wanki Min, Gyeonggi-do (KR)

(73) Assignee: SPECLIPSE, INC., Seoul (KR)

( * ) Notice: Subject to any disclaimer, the term of this patent is extended or adjusted under 35 U.S.C. 154(b) by 0 days.

(21) Appl. No.: 15/258,253

(22) Filed: Sep. 7, 2016

(65) Prior Publication Data
US 2017/0281007 A1    Oct. 5, 2017

(30) Foreign Application Priority Data
Apr. 4, 2016 (KR) .................. 10-2016-0041313

(51) Int. Cl.
  *A61B 5/00*    (2006.01)
  *G01J 3/02*    (2006.01)
  (Continued)

(52) U.S. Cl.
  CPC .......... *A61B 5/0077* (2013.01); *A61B 5/0075* (2013.01); *A61B 5/441* (2013.01);
  (Continued)

(58) Field of Classification Search
  CPC ......... A61B 5/05; A61B 5/00; A61B 5/14532; A61B 5/1455; A61B 5/0059;
  (Continued)

(56) References Cited

U.S. PATENT DOCUMENTS 8,606,350 B2    12/2013 Ishihara .................. 600/476
2013/0079649 A1*    3/2013 Mestha ............... A61B 5/0022
                                                            600/508

(Continued)

FOREIGN PATENT DOCUMENTS

JP            2006-061683    3/2005    ............... A61B 1/00
KR    10-2015-0061218    6/2015    ............... A61B 6/02

OTHER PUBLICATIONS

Office Action dated May 11, 2016, issued in KR 10-2016-0041313.

*Primary Examiner* — Joel Lamprecht
(74) *Attorney, Agent, or Firm* — Harness, Dickey & Pierce, P.L.C.

(57) ABSTRACT

A disease diagnosis and skin age measurement apparatus includes: a first light collection unit; a second light collection unit; a spectrometer configured to measure a spectrum of the light which is collected by the second light collection unit; a spectrum data comparison unit for disease diagnosis configured to compare the spectrum measured by the spectrometer and reference spectrum data for disease diagnosis; a CCD; an image data comparison unit configured to compare the digital image converted by the CCD and a reference image; a disease diagnosis unit configured to determine whether there is a disease in the body tissue; and/or a spectrum data comparison unit for skin age measurement configured to measure skin age by comparing a spectrum measured by the spectrometer and reference spectrum data for skin age measurement, wherein the light projected onto the body tissue is collimate light.

18 Claims, 13 Drawing Sheets

(51) Int. Cl.
*G01J 3/28* (2006.01)
*G01J 3/443* (2006.01)

(52) U.S. Cl.
CPC ............... *G01J 3/021* (2013.01); *G01J 3/024* (2013.01); *G01J 3/0208* (2013.01); *G01J 3/0218* (2013.01); *G01J 3/0248* (2013.01); *G01J 3/0291* (2013.01); *G01J 3/2803* (2013.01); *G01J 3/2823* (2013.01); *G01J 3/443* (2013.01); *A61B 5/7246* (2013.01); *A61B 5/7282* (2013.01); *G01J 2003/282* (2013.01)

(58) Field of Classification Search
CPC ..... A61B 5/0205; A61B 5/113; A61B 5/0077; A61B 5/0075; A61B 5/441; A61B 5/7246
See application file for complete search history.

(56) References Cited

U.S. PATENT DOCUMENTS

| | | | |
|---|---|---|---|
| 2013/0303921 A1* | 11/2013 | Chu | A61B 5/0059 600/473 |
| 2015/0148633 A1 | 5/2015 | Park | A61B 5/14551 |
| 2016/0231235 A1* | 8/2016 | Gulati | A61B 5/02416 |

* cited by examiner

DISEASE DIAGNOSIS AND SKIN AGE MEASUREMENT APPARATUS USING LASER IRRADIATION DEVICE AND DETACHABLE HANDPIECE USED IN THE SAME

CROSS-REFERENCE TO RELATED PATENT APPLICATION

This application claims priority from Korean Patent Application No. 2016-0041313, filed on Apr. 4, 2016 in the Korean Intellectual Property Office, the disclosure of which is incorporated herein by reference in its entirety.

FIELD

Apparatuses and methods consistent with the exemplary embodiments relate to a disease diagnosis and skin age measurement apparatus using a laser irradiation device and a detachable handpiece used in the apparatus, and more particularly, to a disease diagnosis and skin age measurement apparatus using a laser irradiation device for medical or beauty care and a detachable handpiece used in the apparatus.

BACKGROUND

Related-art laser irradiation devices such as a skin toning device, a skin peeling device, or a laser surgery device perform operations for medical or beauty care using lasers.

Among the laser irradiation devices for medical or beauty care as described above, there are devices using collimated beams. The collimated beam has low energy density per unit area and thus cannot be used for other purposes but for medical or beauty purpose.

SUMMARY

One or more aspects of the exemplary embodiments provide a disease diagnosis and skin age measurement apparatus using a laser irradiation device for medical or beauty care.

One or more aspects of the exemplary embodiments also provide a detachable handpiece which is used in a disease diagnosis and skin age measurement apparatus using a laser irradiation device for medical or beauty care.

According to an aspect of an exemplary embodiment, there is provided a disease diagnosis and skin age measurement apparatus for collecting light which is generated when light is projected onto body tissue, and diagnosing a disease, the disease diagnosis and skin age measurement apparatus including: a first light collection unit configured to collect a part of the generated light; a second light collection unit configured to collect a part of the generated light; a spectrometer configured to measure a spectrum of the light which is collected by the second light collection unit; a spectrum data comparison unit for disease diagnosis configured to compare the spectrum measured by the spectrometer and reference spectrum data for disease diagnosis; a CCD configured to convert the light collected by the first light collection unit into a digital image; an image data comparison unit configured to compare the digital image converted by the CCD and a reference image; and a disease diagnosis unit configured to determine whether there is a disease in the body tissue based on at least one of a result of the comparing by the spectrum data comparison unit for disease diagnosis and a result of comparing by the image data comparison unit, wherein the light projected onto the body tissue is collimated light.

According to an aspect of another exemplary embodiment, there is provided a disease diagnosis and skin age measurement apparatus for collecting light which is generated when light is projected onto body tissue, and diagnosing a disease, the disease diagnosis apparatus including: a complex light collection unit configured to collect at least part of the generated light; a spectrometer configured to measure a spectrum of a part of the light which is collected by the complex light collection unit; a spectrum data comparison unit for disease diagnosis configured compare the spectrum measured by the spectrometer and reference spectrum data for disease diagnosis; a CCD configured to convert a part of the light collected by the complex light collection unit into a digital image; an image data comparison unit configured to compare the digital image converted by the CCD and a reference image; and a disease diagnosis unit configured to determine whether there is a disease in the body tissue based on at least one of a result of the comparing by the spectrum data comparison unit for disease diagnosis and a result of the comparing by the image data comparison unit, the light projected onto the body tissue is a collimated beam.

The above-described exemplary embodiments may further include a related data generation unit configured to generate related data which defines a relationship between the digital image converted by the CCD and the spectrum data measured by the spectrometer.

In addition, the above-described exemplary embodiments may further include an SELIES (surface enhanced laser induced emission spectroscopy) film.

In addition, the above-described exemplary embodiments may further include a spectrum data comparison unit for skin age measurement, configured to measure skin age by comparing a spectrum measured by the spectrometer and reference spectrum data for skin age measurement.

According to an aspect of another exemplary embodiment, there is provided a detachable handpiece, which is attachable to or detachable from a laser irradiation device which is able to perform an operation for medical or beauty care using light, the detachable handpiece including: a body part which is formed in a cylindrical shape and has a path formed therein to allow light to travel, and includes a generated light entering part configured to receive light which is generated when light is projected onto body tissue by the laser irradiation device, and a connection part detachably connected with the laser irradiation device; a CCD disposed in the body part to generate a digital image; and a light collection unit configured to split the generated light entering through the generated light entering part into a spectrometer and the CCD, wherein the CCD is configured to generate the digital image corresponding to the light provided from the light collection unit, and wherein the laser projected onto the body tissue by the laser irradiation device is a collimated beam.

According to one or more embodiments of the present disclosure, it is possible to diagnose a disease as well as perform a medical or beauty treatment using a laser irradiation device using a collimated beam, and furthermore, a disease is diagnosed using both a digital image and spectrum data and thus the disease can be diagnosed more exactly.

According to one or more embodiments of the present disclosure, it is possible to diagnose a disease and measure skin age simultaneously, as well as perform a medical or beauty treatment using a laser irradiation device using a collimated beam.

According to one or more embodiments of the present disclosure, it is possible to diagnose a disease as well as perform a medical or beauty treatment using a laser irradiation device using a collimated beam, and furthermore, data relating a digital image and spectrum data can be established.

According to one or more embodiments of the present disclosure, by connecting a handpiece according to an exemplary embodiment without changing a configuration of a related-art laser irradiation device, it is possible to diagnose a disease as well as perform a medical or beauty treatment.

According to one or more embodiments of the present disclosure, even when the sensitivity of a signal of generated light is weak, a disease can be diagnosed using an SELIES film.

Additional aspects and advantages of the exemplary embodiments will be set forth in the detailed description, will be obvious from the detailed description, or may be learned by practicing the exemplary embodiments.

BRIEF DESCRIPTION OF THE DRAWINGS

The above and other features and advantages will become more apparent by describing in detail exemplary embodiments with reference to the attached drawings in which.

DETAILED DESCRIPTION

Exemplary embodiments will now be described more fully with reference to the accompanying drawings to clarify aspects, other aspects, features and advantages of the inventive concept. The exemplary embodiments may, however, be embodied in many different forms and should not be construed as limited to the exemplary embodiments set forth herein. Rather, the exemplary embodiments are provided so that this disclosure will be thorough and complete, and will fully convey the scope of the application to those of ordinary skill in the art. It will be understood that when an element is referred to as being "on" another element, the element can be directly on another element or intervening elements.

The terms "unit", "module", or the terms having suffix "-er or -or" used in the following description refers to a unit for processing at least one function or operation, and may be implemented by hardware, software, or a combination of hardware and software.

The terms used herein are for the purpose of describing particular exemplary embodiments only and are not intended to be limiting. As used herein, the singular forms are intended to include the plural forms as well, unless the context clearly indicates otherwise. It will be further understood that the terms "comprises" and/or "comprising," when used in this specification, do not preclude the presence or addition of one or more other components.

Definition of Terms

In the following description, the expression "a laser (or light or a collimated beam) is provided (or enters or is output) from one element (A) to another element (B)" is used to mean that a laser (or light or a collimated beam) is directly provided from one element (A) to another element (B) or a laser (or light or a collimated beam) outputted from one element (A) is provided to another element (B) through at least one optical device.

The term "laser" used in the following description means a pulsed laser or a continuous wave laser. In addition, the frequency band of the "laser" may have a certain frequency band, for example, a ultra violet (UV) band, a visible light band, or an infra-red (IR) band.

The term "generated light" used in the following description encompasses all types of light which are generated when a laser is projected onto body tissue. Accordingly, the "generated light" may mean absorbed light, reflected light, scattered light, electronic emission light and/or fluorescent light from the tissue.

Figure 1:
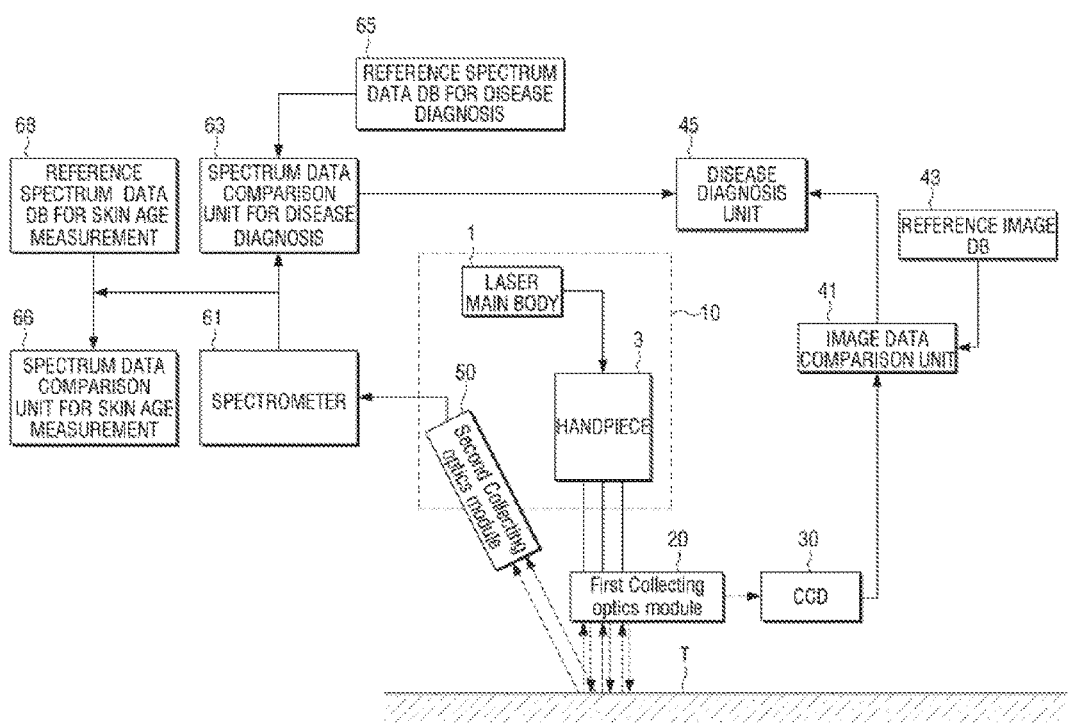
FIG. 1 is a view to illustrate a disease diagnosis and skin age measurement apparatus according to an exemplary embodiment of the present disclosure.

FIG. 1 is a view to illustrate a disease (including cancer, and other different types of disease) diagnosis and skin age (the level of collagen or elastin concentration) measurement apparatus according to an exemplary embodiment of the present disclosure.

Referring to FIG. 1, the disease diagnosis and skin age measurement apparatus according to an exemplary embodiment of the present disclosure may be used with a laser irradiation device using light (hereinafter, referred to as a "laser irradiation device").

In this embodiment, the laser irradiation device 10 is a device which performs operations for medical or beauty care using light. The laser irradiation device 10 may be a device using a laser, such as a skin toning device, a skin peeling device, or a laser surgery device. The above-described devices are merely examples of the laser irradiation device 10 and the laser irradiation device 10 is not limited to the above-described devices.

The laser irradiation device 10 projects a collimated beam onto body tissue (T), and the disease diagnosis and skin age measurement apparatus according to an exemplary embodiment of the present disclosure may collect light which is generated when light is projected onto the body tissue (T) and determine whether there is a disease in the body tissue (T), and may measure skin age when the body tissue (T) is skin. The collimated beam may be referred to as parallel light or collimate light in the technical field to which the present disclosure belongs.

The spot size of the collimated beam may be a few micrometers to a few millimeters, for example. This is the size of the collimated beam required to excite or ablate the tissue and obtain a digital image.

The spot size of the collimated beam should be large enough to generate a digital image. However, such a large spot size may decrease energy density transmitted to the body tissue and thus reduce the intensity of the generated light. Accordingly, the size of the collimated beam should be maintained so as to generate the digital image, and also, should be small enough to provide a sufficient spectrum signal. To achieve this, the intensity of the generated light may be increased by using a Surface Enhanced Laser Induced Emission Spectroscopy (SELIES) film in this embodiment.

The disease diagnosis and skin age measurement apparatus according to an exemplary embodiment of the present disclosure may determine whether there is a disease in the tissue (T) and/or may measure skin age, based on a spectrum data and an image of the generated light that is generated when light is projected onto the body tissue (T).

In this embodiment, the laser irradiation device 10 may include a laser main body 1 for generating a laser, and a handpiece 3 for projecting the laser. Although not shown in FIG. 1, a collimator may be provided in the laser main body 1 or the handpiece 3 to convert the laser generated by the laser main body 1 into a collimated beam.

The disease diagnosis and skin age measurement apparatus according to an exemplary embodiment of the present disclosure, which is used with the laser irradiation device 10, may include a first light collection unit 20, a Charge Coupled Device (CCD) 30, an image data comparison unit 41, a reference image database (DB) 43 which stores reference images, a disease diagnosis unit 45, a second light collection unit 50, a spectrometer 61, a spectrum data comparison unit for disease diagnosis 63, a reference spectrum data DB 65 for disease diagnosis which stores reference spectrum data for disease diagnosis, a spectrum data comparison unit 66 for skin age measurement, and a reference spectrum data DB 68 for skin age measurement, which stores reference spectrum data for skin age measurement. At least some of the elements included in the disease diagnosis and skin age measurement apparatus according to an exemplary embodiment of the present disclosure may be connected to the laser irradiation device 10 or may be disposed in the proximity of the laser irradiation device 10.

In this embodiment, the first light collection unit 20 may collect at least part of the light which is generated when light is projected onto the body tissue (T). The generated light which is collected by the first light collection unit 20 may be a collimated beam, and the collimated beam is provided to the CCD 30.

The CCD 30 converts the collimated beam provided by the first light collection unit 20 into a digital image.

The image data comparison unit 41 compares the digital image (hereinafter, referred to as "target image") converted by the CCD 30, and reference images stored in the reference image DB 43.

Specifically, the image data comparison unit 41 finds an image which is the same as or similar to the target image from among the reference images stored in the reference image DB 43. Herein, a criterion for determining similarity of the image may be appropriately determined by a person skilled in the art.

The image data comparison unit 41 may compare the target image and the reference images and then provide the score of similarity between the target image and the reference images to show the result as "matched" or "mismatched." Alternatively, the image data comparison unit 41 may show the result as "matched," "similar," or "mismatched." Herein, the result "matched" indicates that there is a reference image matching the target image by more than 90%, the result "similar" indicates that there is a reference image matching the target image by 80-90%, and the result "mismatched" indicates that there is a reference image matching the target image by 0-80%.

The numerical values used herein are merely an example and may be differently defined by a person skilled in the art.

Meanwhile, the result of the comparing by the image data comparison unit 41 is provided to the disease diagnosis unit 45.

In this embodiment, the second light collection unit 50 may collect at least part of the light which is generated when light is projected onto the body tissue (T). That is, one part of the light which is generated when light is projected onto the body tissue (T) is collected by the first light collection unit 20, and another part of the generated light is collected by the second light collection unit 50.

The generated light which is collected by the second light collection unit 50 is provided to the spectrometer 61 via an optical fiber.

The spectrometer 61 measures the spectrum of the light provided by the second light collection unit 50, and the result of measuring the spectrum by the spectrometer 61 is provided to the spectrum data comparison unit 63 for disease diagnosis.

The spectrum data comparison unit 63 for disease diagnosis compares the spectrum data (hereinafter, "target spectrum") provided by the spectrometer 61 and reference spectrum data stored in the reference spectrum data DB 65 for disease diagnosis.

The spectrum data comparison unit for disease diagnosis 63 finds reference spectrum data for disease diagnosis which is the same as or similar to the target spectrum among the reference spectrum data stored in the reference spectrum data DB 65 for disease diagnosis. Herein, a criterion for determining similarity of the spectrum data may be appropriately determined by a person skilled in the art.

The spectrum data comparison unit 63 for disease diagnosis may compare the target spectrum and the reference spectrum data for disease diagnosis and then provide the score of similarity between the target spectrum and the reference spectrum to show the result as "matched" or "mismatched." Alternatively, the spectrum data comparison unit 63 for disease diagnosis may show the result as "matched," "similar," or "mismatched." Herein, the result "matched" indicates that there is a reference spectrum data for disease diagnosis matching the target spectrum by more than 90%, the result "similar" indicates that there is a reference spectrum data for disease diagnosis matching the target spectrum by 80-90%, and the result "mismatched" indicates that there is a reference spectrum data for disease diagnosis matching the target spectrum by 0-80%. The numerical values used herein are merely an example and may be differently defined by a person skilled in the art. The result of the comparing by the spectrum data comparison unit 63 for disease diagnosis is provided to the disease diagnosis unit 45.

The disease diagnosis unit 45 determines whether there is a disease in the body tissue (T) based on the result of the comparing by the spectrum data comparison unit 63 for disease diagnosis and the result of the comparing by the image data comparison unit 41.

For example, the disease diagnosis unit 45 may determine whether there is a disease in the body tissue (T) in one of the following methods i) to iii):

i) The disease diagnosis unit 45 determines that there is a disease only when the result of the comparison of the spectrum data indicates "matched" and the result of the comparison of the image data indicates "matched."

ii) The disease diagnosis unit 45 determines that there is a disease when either the result of the comparison of the spectrum data or the result of the comparison of the image data indicates "matched."

iii) The disease diagnosis unit 45 determines that there is a disease when one of the result of the comparison of the spectrum data and the result of the comparison of the image data indicates "matched" and the other one indicates "similar."

Herein, the methods i) to iii) are merely examples and the disease diagnosis unit 45 may determine whether there is a disease or not in other methods.

The spectrum data comparison unit 66 for skin age measurement may measure skin age by analyzing a spectrum measured by the spectrometer 61. There is a change in the spectrum when there is a change in chemical components, such as a change in a collagen or elastin component in skin. The spectrum data comparison unit 66 for skin age measurement may measure skin age by measuring the changes in the level of the collagen or elastin concentration from the spectrum. For example, the spectrum data comparison unit 66 for skin age measurement may measure skin age by comparing the spectrum measured by the spectrometer 61 with the reference spectrum data DB 68 for skin age measurement. The reference spectrum data for skin age measurement may be relating the skin age and the emission spectrum.

Figure 2A:
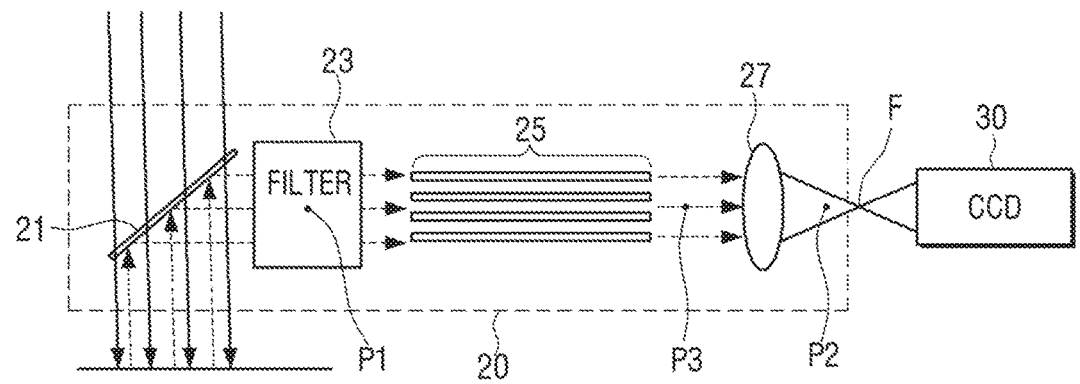
FIGS. 2A and 2B are views to illustrate a first light collection unit according to an exemplary embodiment of the present disclosure.
Figure 2B:
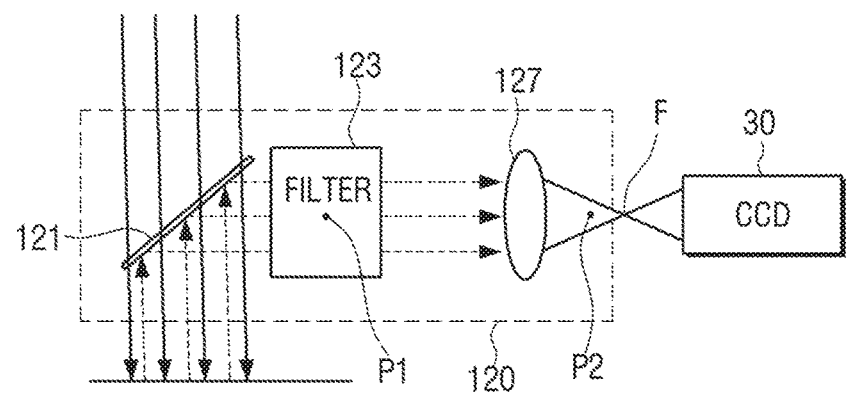

FIGS. 2A and 2B are views to illustrate a first light collection unit according to an exemplary embodiment. Specifically, FIG. 2A illustrates a first light collection unit according to an exemplary embodiment of the present disclosure, and FIG. 2B illustrates a first light collection unit according to another exemplary embodiment of the present disclosure.

The configurations of the first light collection units shown in FIGS. 2A and 2B are examples of the first light collection unit 20 explained in the embodiment of FIG. 1.

Referring to FIG. 2A, the first light collection unit 20 includes an optical module which provides at least part of the generated light which is collected by the first light collection unit 20 to the CCD 30.

In this embodiment, the optical module may include an optical device 21 for changing the direction of at least part of the generated light, a filter 23 which receives light the direction of which has been changed by the optical device 21 and outputs only the light of a specific spectral band, an optical fiber bundle 25 which receives the light outputted from the filter 23, and an optical device 27 which receives the light delivered by the optical fiber bundle and provides the light to the CCD 30. Herein, the filter 23 may be disposed on any location of P1 (between the optical device 21 and the optical fiber bundle 25), P2 (between the CCD 30 and the optical device 27), or P3 (between the optical device 27 and the optical fiber bundle 25).

Referring to FIG. 2B, the first light collection unit 120 includes an optical module which provides at least part of the generated light which is collected by the first light collection unit 120 to the CCD 30. In this embodiment, the optical module may include an optical device 121 for changing the direction of at least part of the generated light, a filter 123 which receives light the direction of which has been changed by the optical device 121 and outputs only the light of a specific spectral band, and an optical device 127 which receives the light emitted by the filter 123 and provides the light to the CCD 30. Herein, the filter 23 may be disposed on any location of P1 (between the optical device 121 and the optical device 127) and P2 (between the CCD 30 and the optical device 127).

The optical devices 21 and 121 in the embodiment explained with reference to FIGS. 2A and 2B may be configured not to influence the collimated beam which is projected onto the body tissue from the laser irradiation device, as shown in FIGS. 2A and 2B. In FIGS. 2A and 2B, "F" indicates a focusing location.

Figure 3A:
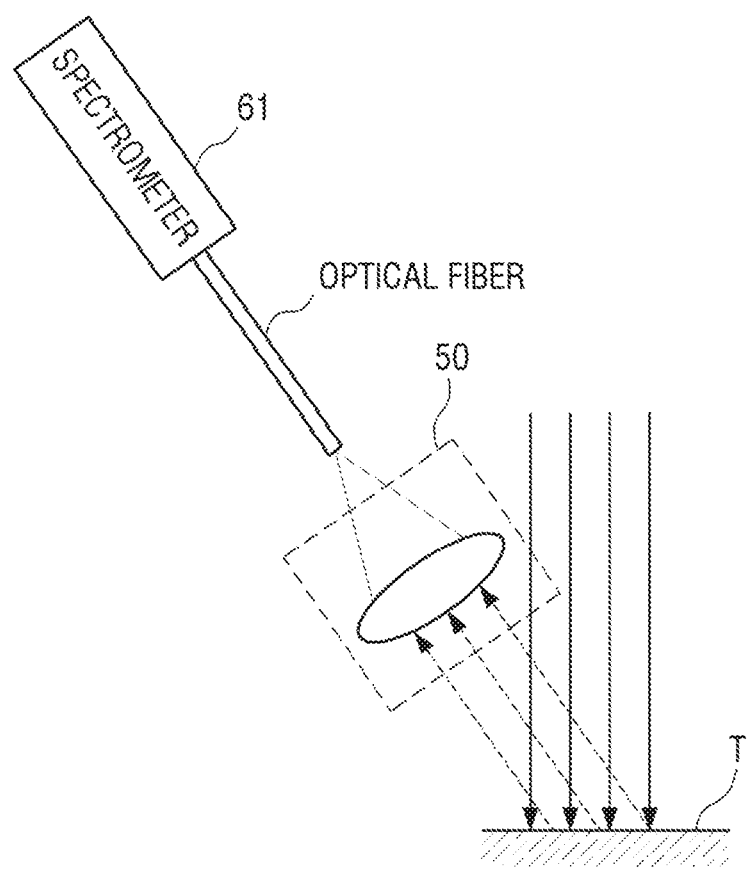
FIGS. 3A and 3B are views to illustrate a second light collection unit according to an exemplary embodiment of the present disclosure.
Figure 3B:
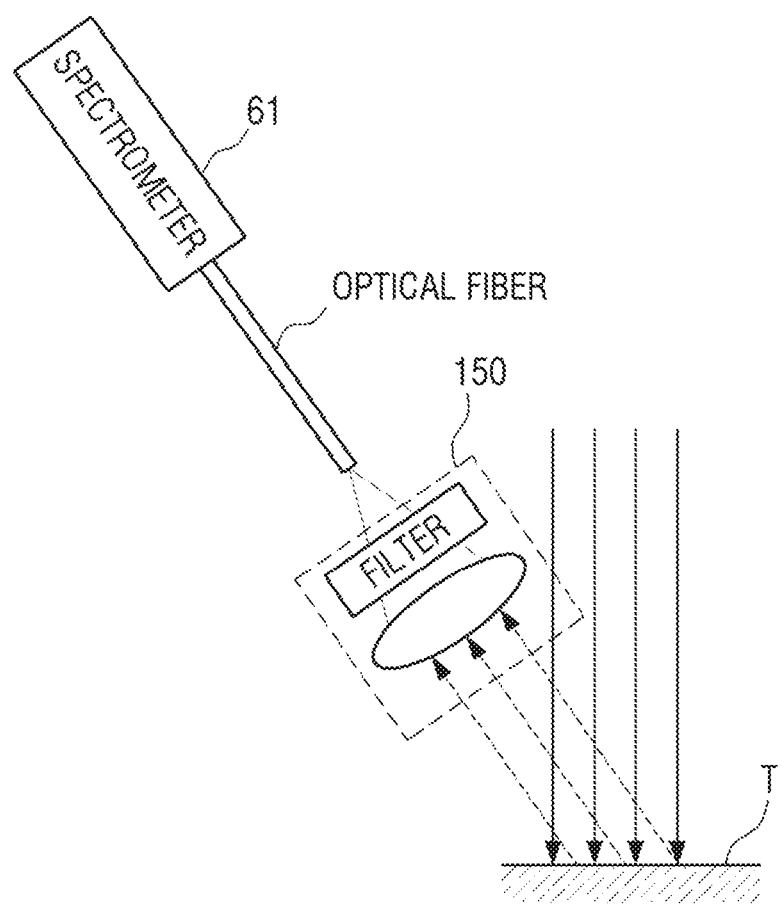

FIGS. 3A and 3B are views to illustrate a second light collection unit according to an exemplary embodiment of the present disclosure. Specifically, FIG. 3A illustrates a second light collection unit according to an exemplary embodiment of the present disclosure, and FIG. 3B illustrates a second light collection unit according to another exemplary embodiment of the present disclosure. The second light collection units shown in FIGS. 3A and 3B are exemplary configurations of the second light collection unit 50 explained in the embodiment of FIG. 1.

Referring to FIG. 3A, the second light collection unit 50 includes an optical module which provides at least part of the generated light which is collected by the second light collection unit 50 to the spectrometer 61. Herein, the optical module may provide the generated light which is collected by the optical module to an optical fiber connected to the spectrometer 61. In this embodiment, the optical module may include an optical device (for example, a lens) which receives at least part of the generated light and provides the part of the generated light to the optical fiber connected to the spectrometer 61.

Referring to FIG. 3B, the second light collection unit 150 includes an optical module which provides at least part of the generated light which is collected by the second light collection unit 150 to the spectrometer 61. In this embodiment, the optical module may include an optical device and a filter. The optical device receives at least part of the generated light and provides the part of the generated light to the filter, and the filter filters out light of a specific spectral band from the generated light and then provides the filtered light to the spectrometer 61.

Figure 4:
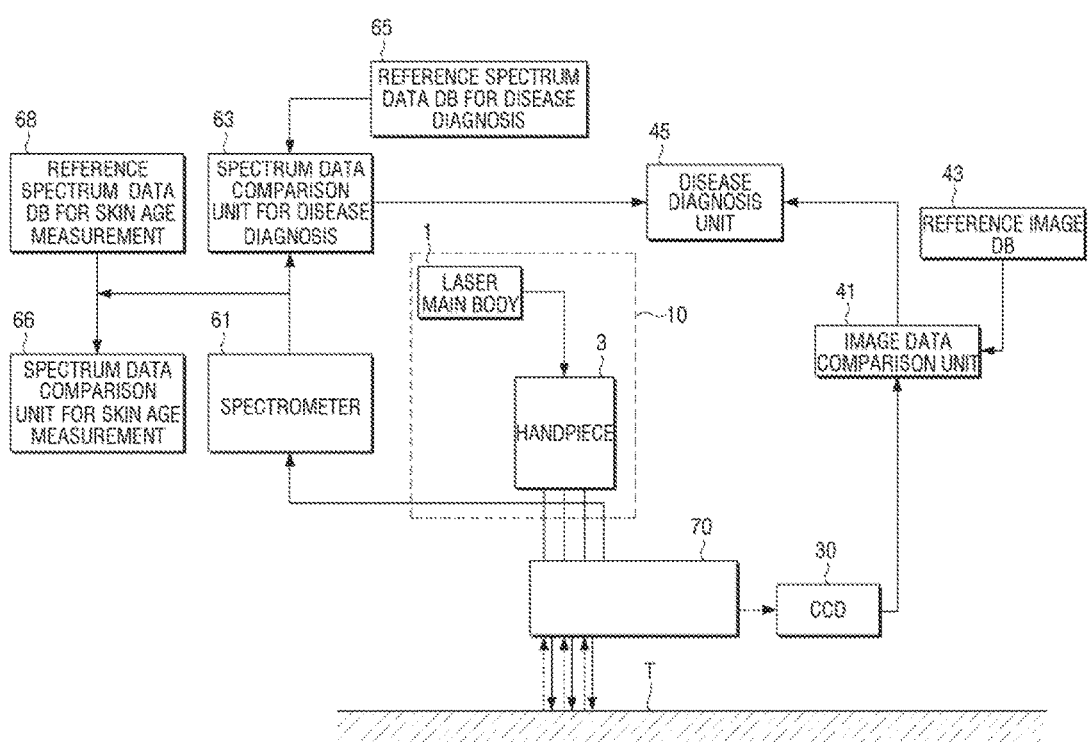
FIG. 4 is a view to illustrate a disease diagnosis and skin age measurement apparatus according to another exemplary embodiment of the present disclosure.

FIG. 4 is a view to illustrate a disease diagnosis and skin age measurement apparatus according to another exemplary embodiment of the present disclosure.

Referring to FIG. 4, the disease diagnosis and skin age measurement apparatus according to another exemplary embodiment of the present disclosure may be used with a laser irradiation device. The laser irradiation device 10 projects a collimated beam onto body tissue (T) as described above with reference to FIG. 1.

The disease diagnosis and skin age measurement apparatus according to another exemplary embodiment of the present disclosure may include a CCD 30, an image data comparison unit 41, a reference image DB 43 which stores reference images, a disease diagnosis unit 45, a spectrometer 61, a spectrum data comparison unit for disease diagnosis 63, a reference spectrum data DB 65 for disease diagnosis which stores reference spectrum data for disease diagnosis, a reference spectrum data DB 68 for skin age measurement, which stores reference spectrum data for skin age measurement, a complex light collection unit 70, and a spectrum data comparison unit 66 for skin age measurement. At least some of the elements included in the disease diagnosis and skin age measurement apparatus according to an exemplary embodiment of the present disclosure may be connected to the laser irradiation device 10 or may be disposed in the proximity of the laser irradiation device 10.

Comparing the disease diagnosis and skin age measurement apparatus shown in FIG. 1 and the disease diagnosis and skin age measurement apparatus shown in FIG. 4, there is a difference in that the disease diagnosis and skin age measurement apparatus shown in FIG. 1 includes the first light collection unit 20 and the second light collection unit 50, whereas the disease diagnosis and skin age measurement apparatus shown in FIG. 4 includes the complex light collection unit 70. Hereinafter, the embodiment of FIG. 4 will be explained based on the difference.

Referring to FIG. 4, the complex light collection unit 70 collects light which is generated when light is projected onto the body tissue (T), and splits the collected light into the CCD 30 and the spectrometer 61. That is, the complex light collection unit 70 provides one part of the collected light to the CCD 30 and provides another part of the light to the spectrometer 61.

The complex light collection unit 70 collects a collimated beam and provides a part of the collected collimated beam to the CCD 30.

The CCD 30 converts the light provided by the complex light collection unit 70 into a digital image, and provides the digital image to the image data comparison unit 41.

The spectrometer 61 measures a spectrum of the light provided by the complex light collection unit 70, and provides the measured spectrum to the spectrum data comparison unit 63 for disease diagnosis.

Regarding the image data comparison unit 41, the reference image DB 43, the disease diagnosis unit 45, the spectrum data comparison unit 63 for disease diagnosis, the reference spectrum data DB 65 for disease diagnosis, and the reference spectrum data DB 68 for skin age measurement, and the spectrum data comparison unit 66 for skin age measurement of FIG. 4, please refer to the explanation of the embodiment of FIG. 1.

Figure 5A:
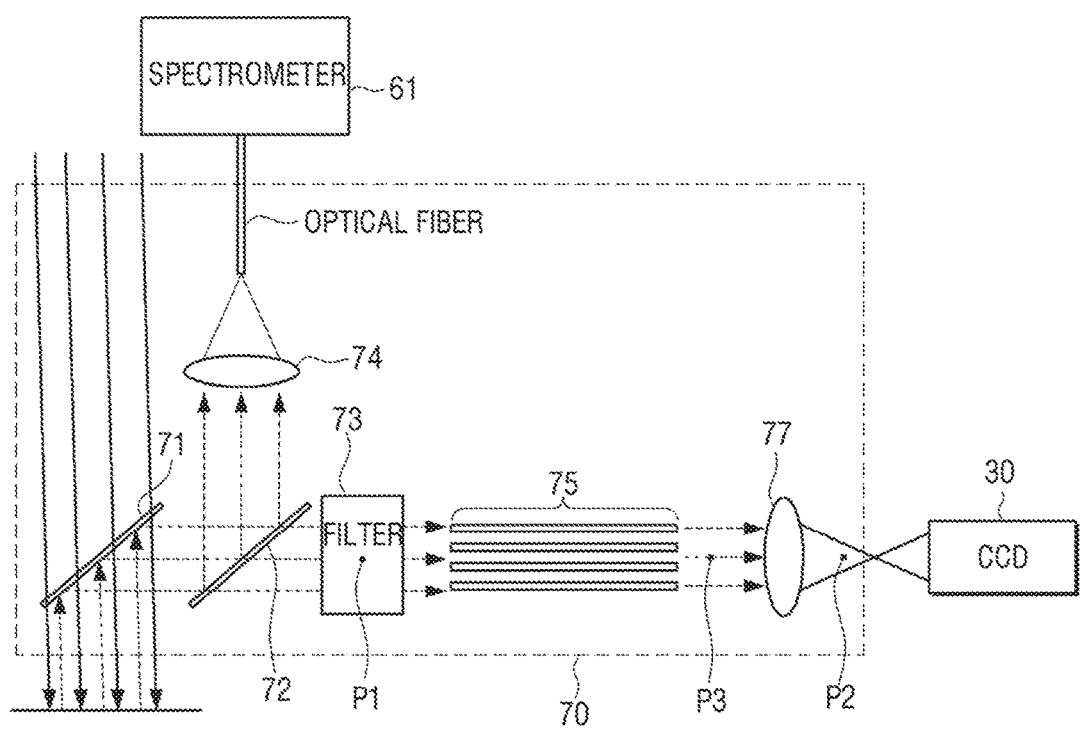
FIGS. 5A, 5B, 6A, and 6B are views to illustrate a complex light collection unit according to an exemplary embodiment of the present disclosure.
Figure 5B:
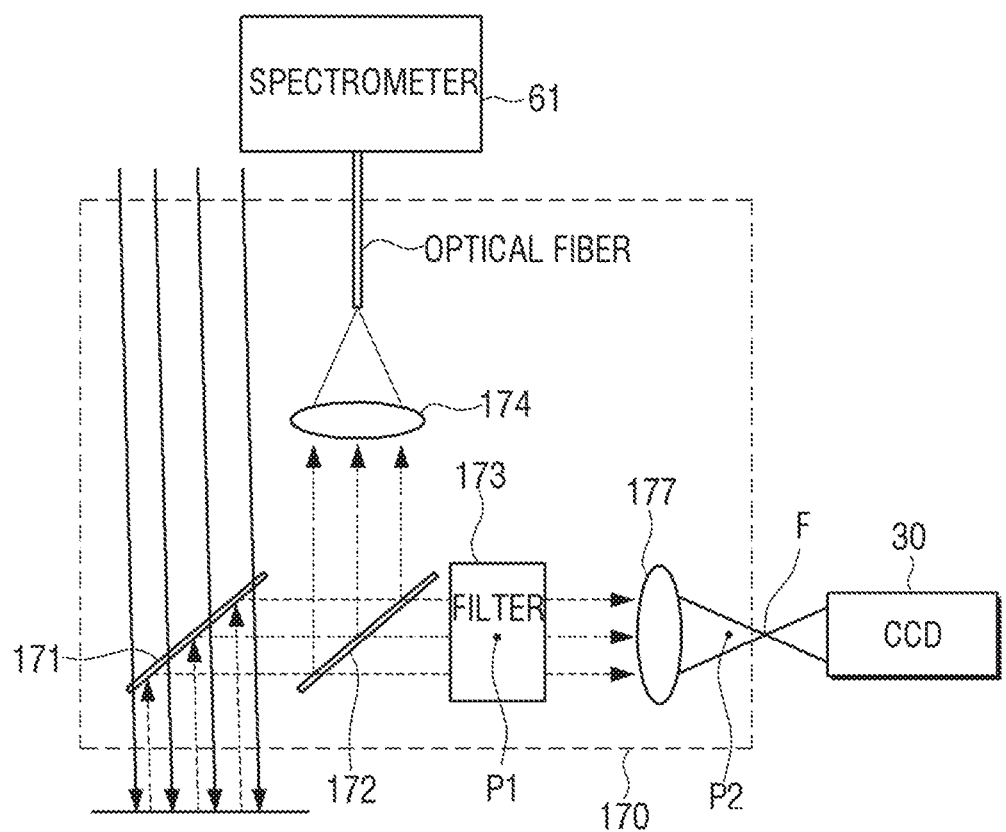
Figure 6A:
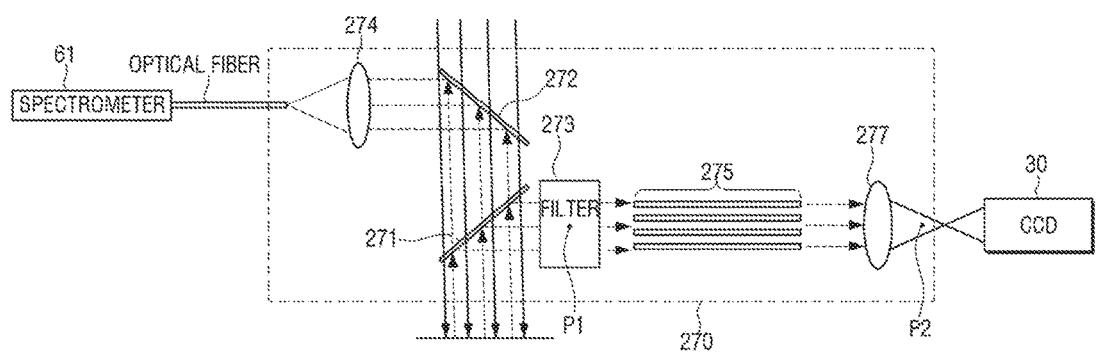
Figure 6B:
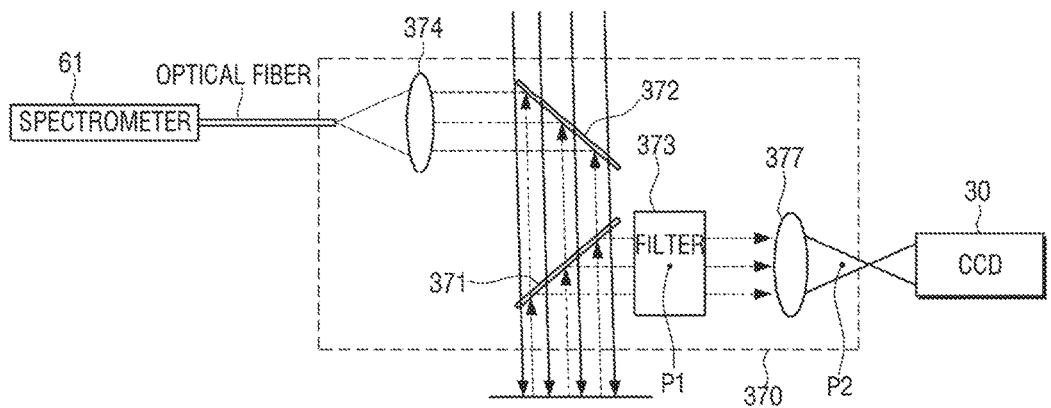

FIGS. 5A and 5B and FIGS. 6A and 6B are views to illustrate a complex light collection unit according to exemplary embodiments of the present disclosure. Specifically, FIG. 5A illustrates a complex light collection unit according to an exemplary embodiment of the present disclosure, FIG. 5B illustrates a complex light collection unit according to another exemplary embodiment of the present disclosure, FIG. 6A illustrates a complex light collection unit according to another exemplary embodiment of the present disclosure, and FIG. 6B illustrates a complex light collection unit according to another exemplary embodiment of the present disclosure.

The complex light collection units illustrated in FIGS. 5A to 6B are exemplary configurations of the complex light collection unit 70 explained in the embodiment of FIG. 4. The complex light collection units illustrated in FIGS. 5A to 6B split the light which is generated when light is projected onto the body tissue (T) into the CCD 30 and the spectrometer 61. That is, the complex light collection units illustrated in FIGS. 5A to 6B provide one part of the collected light to the CCD 30 and provide another part of the collected light to the spectrometer 61.

In addition, the complex light collection units shown in FIGS. 5A to 6B each includes a first optical module which receives the generated light, and splits the light into a first direction and a second direction and transmits the split light, a second optical module which receives at least part of the light transmitted in the first direction, and a third optical module which receives at least part of the light transmitted in the second direction. The second optical module provides the at least part of the light provided from the first optical module to an optical fiber connected to the spectrometer 61, and the third optical module provides the at least part of the light provided from the first optical module to the CCD 30.

Referring to FIG. 5A, the first optical module of the complex light collection unit 70 includes two optical devices 71 and 72. For example, the optical device 71 receives at least part of the generated light, and changes the direction of the generated light and provides the light to the optical device 72. The optical device 72 splits the light provided from the optical device 71 into the second optical module and the third optical module, and transmits the light.

The second optical module of the complex light collection unit 70 includes an optical device 74 which provides the light provided from the optical device 72 to the optical fiber. The optical device 74 may be a lens, for example.

The third optical module of the complex light collection unit 70 may include three optical devices 73, 75, and 77. For example, the optical device 73 is a filter which filters out light of a specific spectral band from the light provided from the optical device 72, the optical device 75 is an optical fiber bundle 75 which receives the light filtered by the optical device 73 and provides the light to the optical device 77, and the optical device 77 is a lens which provides the light received from the optical fiber bundle 75 to the CCD 30.

Referring to FIG. 5B, the first optical module of the complex light collection unit 170 includes two optical devices 171 and 172. For example, the optical device 171 receives at least part of the generated light, and changes the direction of the generated light and provides the light to the optical device 172. The optical device 172 splits the light received from the optical device 171 into the second optical module and the third optical module, and transmits the light.

The second optical module of the complex light collection unit 170 includes an optical device 174 which provides the light received from the optical device 172 to an optical fiber. The optical device 174 may be a lens, for example.

The third optical module of the complex light collection unit 170 includes two optical devices 173 and 177. For example, the optical device 173 is a filter which filters out light of a specific spectral band from the light provided from the optical device 172, and the optical device 177 is a lens which provides the light received from the optical device 173 to the CCD 30.

Referring to FIG. 6A, the first optical module of the complex light collection unit 270 includes two optical devices 271 and 272. For example, the optical device 271 is disposed to receive at least part of the generated light, and splits the generated light and provides the light to the optical device 272 and the third optical module. The optical device 272 provides the light received from the optical device 271 to the second optical module.

The second optical module of the complex light collection unit 270 includes an optical device 274 which provides the light received from the optical device 272 to an optical fiber. The optical device 274 may be a leans, for example.

The third optical module of the complex light collection unit 270 may include three optical devices 273, 275, and 277. For example, the optical device 273 is a filter which filters out light of a specific spectral band from the light provided from the optical device 271, the optical device 275 is an optical fiber bundle 275 which receives the light filtered by the optical device 273 and provides the light to the optical device 277, and the optical device 277 is a lens which provides the light received from the optical fiber bundle 275 to the CCD 30.

Referring to FIG. 6B, the first optical module of the complex light collection unit 370 includes two optical devices 371 and 372. For example, the optical device 371 receives at least part of the generated light, and splits the generated light and transmits the light to the optical device 372 and the third optical module. The optical device 372 provides the light received from the optical device 371 to the second optical module.

The second optical module of the complex light collection unit 370 includes an optical device 374 which provides the light received from the optical device 372 to an optical fiber. The optical device 374 may be a lens, for example.

The third optical module of the complex light collection unit 370 may include two optical devices 373 and 377. For example, the optical device 373 is a filter which filters out light of a specific spectral band from the light provided from the optical device 371, and the optical device 377 is a lens which provides the light received from the optical device 373 to the CCD 30.

The optical devices 71, 171, 271, 272, 371, 372 in the exemplary embodiments described with reference to FIGS. 5A to 6B each is configured not to influence the collimated beam which is projected onto the body tissue from each of medical treatment devices.

Figure 7:
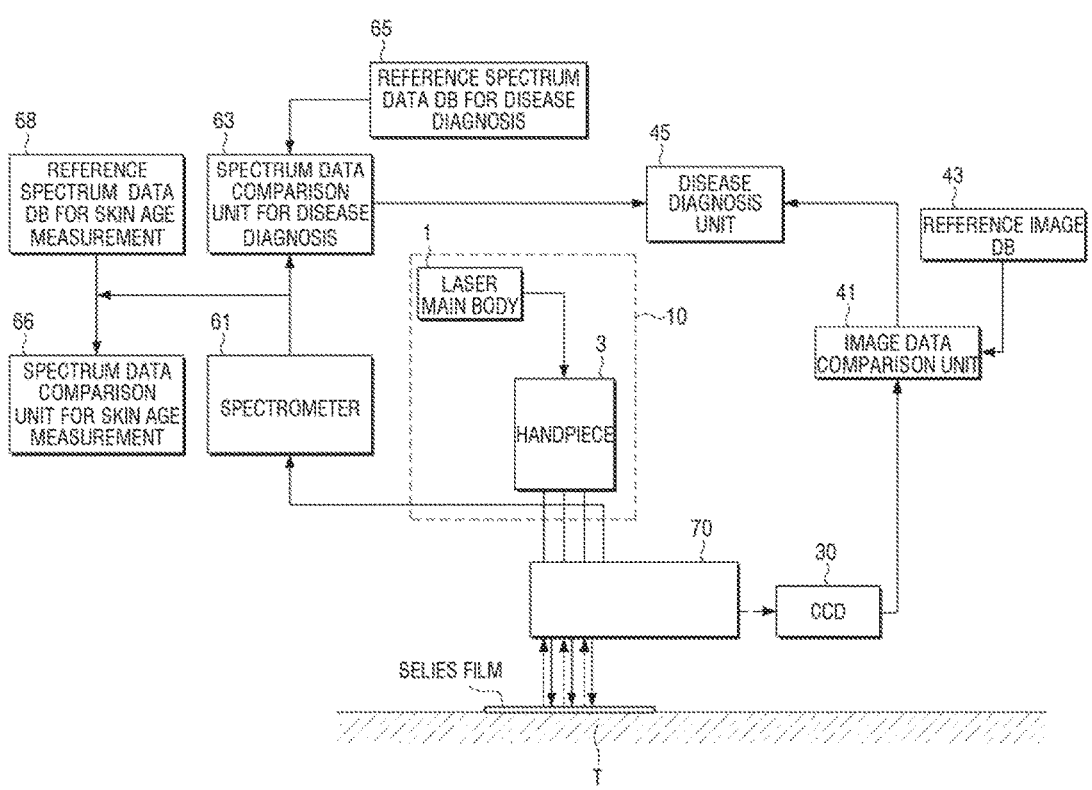
FIG. 7 is a view to illustrate a disease diagnosis and skin age measurement apparatus using Surface Enhanced Laser Induced Emission Spectroscopy (SELIES) according to an exemplary embodiment of the present disclosure.

FIG. 7 is a view to illustrate a disease diagnosis and skin age measurement apparatus using SELIES according to an exemplary embodiment of the present disclosure.

Referring to FIG. 7, the disease diagnosis and skin age measurement apparatus using the SELIES according to an exemplary embodiment of the present disclosure may be used with a laser irradiation device. The laser irradiation device 10 projects a collimated beam onto body tissue (T) as described above with reference to FIG. 1.

The disease diagnosis and skin age measurement apparatus using the SELIES according to an exemplary embodiment of the present disclosure may include a CCD 30, an image data comparison unit 41, a reference image DB 43 which stores reference images, a disease diagnosis unit 45, a spectrometer 61, a spectrum data comparison unit 63 for disease diagnosis, a reference spectrum data DB 65 for disease diagnosis which stores reference spectrum data for disease diagnosis, a reference spectrum data DB 68 for skin age measurement, a complex light collection unit 70, an SELIES film, and a spectrum data comparison unit 66 for skin age measurement. At least some of the elements included in the disease diagnosis and skin age measurement apparatus using the SELIES according to an exemplary embodiment of the present disclosure may be connected to the laser irradiation device 10 or may be disposed in the proximity of the laser irradiation device 10.

Comparing the disease diagnosis and skin age measurement apparatus shown in FIG. 4 and the disease diagnosis and skin age measurement apparatus shown in FIG. 7, there is a difference in that the disease diagnosis and skin age measurement apparatus shown in FIG. 7 further includes the SELIES film, and the complex light collection unit 70 collects generated light which passes through the SELIES film. Hereinafter, the embodiment of FIG. 7 will be explained based on the difference.

Referring to FIG. 7, the SELIES film has a function of enhancing a signal intensity of the generated light, and a structure may be formed on at least one surface of the SELIES film to enhance the light which is generated when light is projected onto body tissue.

The SELIES film may be formed of transparent polymer, for example, and metal particles having a nano or micro size (a few nanometers to a few hundred micrometers) may be formed on a polymer surface. Herein, the transparent polymer is material through which UV light, visible ray, and/or IR light can pass.

In this embodiment, the SELIES film may be formed on the surface of the body tissue (T). To achieve this, the SELIES film may be formed to be attachable to or detachable from skin.

The SELIES film used in the embodiments of the present disclosure may be configured in various forms.

For example, a substrate (hereinafter, referred to as a "substrate for SELIES") which is suitable to be used as the SELIES film may be prepared, and the surface of the substrate for SELIES may be treated to have surface roughness of a nano or micro size (i.e., a few nanometers to a few hundred micrometers). For example, the surface of the substrate for SELIES may have such a surface roughness by placing metallic particles with a nano or micro size on the surface of the substrate for SELIES in a physical or chemical method. In another example, a layer for enhancing the signal intensity of the generated light (hereinafter, referred to as an "light-enhancing layer") may be temporarily or fixedly formed on the surface of the substrate for SELIES. Herein, the light-enhancing layer may be made of material including fine particles.

For example, to temporarily form the light-enhancing layer, material which is able to increase the signal intensity of the generated light may be sprayed or coated onto the surface of the substrate for SELIES. The SELIES film formed in this method may be required to be cleaned after the film is used in a medical and beauty system which can diagnose a disease based on a pulsed laser according to an exemplary embodiment, and can be reused by spraying or coating the material having the fine particles onto the surface of the cleaned substrate for SELIES.

On the other hand, the light-enhancing layer may be fixedly formed by spraying or coating the material having the fine structure onto the surface of the substrate for SELIES and then curing the substrate.

The medical and beauty system which can diagnose a disease based on a pulsed laser according to an exemplary embodiment of the present disclosure may not use the SELIES film and may directly spray or coat the material having the fine structure onto body tissue. That is, the material having the fine structure (material to increase generated light) may be directly sprayed or coated onto the body tissue, and in this state, the laser may be projected and generated light may be collected. The method for forming the SELIES film described above and the method for directly spraying or coating the material having the fine structure onto the body tissue without using the SELIES film may be applied to exemplary embodiments which will be described below with reference to the other drawings.

In this embodiment, the complex light collection unit 70 collects the generated light which passes through the SELIES film, and splits the collected light and transmits the light to the CCD 30 and the spectrometer 61.

In this embodiment, the complex light collection unit 70 collects the collimated beam and provides a part of the collected collimated beam to the spectrometer 61 in the form of a collimated beam.

Figure 8:
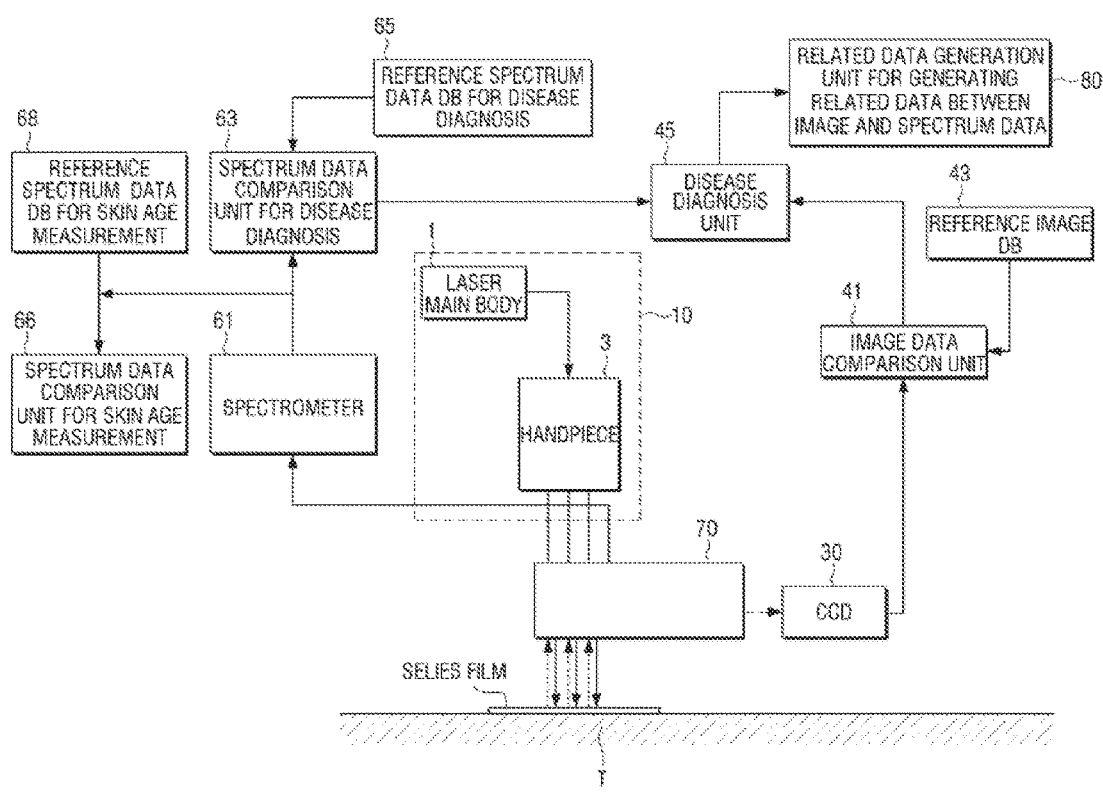
FIG. 8 is a view to illustrate a disease diagnosis and skin age measurement apparatus according to another exemplary embodiment of the present disclosure.

FIG. 8 is a view to illustrate a disease diagnosis and skin age measurement apparatus according to another exemplary embodiment of the present disclosure.

Referring to FIG. 8, the disease diagnosis and skin age measurement apparatus according to another exemplary embodiment of the present disclosure may be used with a laser irradiation device. The laser irradiation device 10 projects a collimated beam onto body tissue (T) as described above with reference to FIG. 1.

The disease diagnosis and skin age measurement apparatus using the SELIES according to an exemplary embodiment of the present disclosure may include a CCD 30, an image data comparison unit 41, a reference image DB 43 which stores reference images, a disease diagnosis unit 45, a spectrometer 61, a spectrum data comparison unit 63 for disease diagnosis, a reference spectrum data DB 65 for disease diagnosis, which stores reference spectrum data for disease diagnosis, a spectrum data DB 68 for skin age measurement, a complex light collection unit 70, an SELIES film, a spectrum data comparison unit 66 for skin age measurement, and a related-data generation unit 80 which generates related data between an image and spectrum data. At least some of the elements included in the disease diagnosis and skin age measurement apparatus according to an exemplary embodiment of the present disclosure may be connected to the laser irradiation device 10 or may be disposed in the proximity of the laser irradiation device 10.

Comparing the disease diagnosis and skin age measurement apparatus shown in FIG. 7 and the disease diagnosis and skin age measurement apparatus shown in FIG. 8, there is a difference in that the disease diagnosis and skin age measurement apparatus shown in FIG. 8 further includes the related-data generation unit 80 which generates related data between an image and spectrum data. Hereinafter, the embodiment of FIG. 8 will be explained based on the difference.

Referring to FIG. 8, the related data generation unit 80 generates related data which defines a relationship between a target image and a target spectrum. That is, the related-data generation unit 80 generates related data which defines a relationship between a digital image generated from the generated light which is split by the complex light collection unit 70, and spectrum data.

For example, the related data is defined to include the digital image (or data indicating a characteristic of such a digital image) which is generated by the CCD 30, a spectrum (data indicating a characteristic of such a spectrum) which is measured by the spectrometer 61, a result of comparing by the spectrum data comparison unit for disease diagnosis, a result of comparing by the image data comparison unit, and a determination made by the disease diagnosis unit.

In the embodiment of FIG. 8 described above, the related data generation unit which generates the related data between the image and the spectrum data is implemented in the form of an additional element added to the embodiment of FIG. 7. However, this is merely an example. The related data generation unit may be implemented in the form of an additional element added to the embodiment of FIG. 1 or the embodiment of FIG. 4.

Figure 9A:
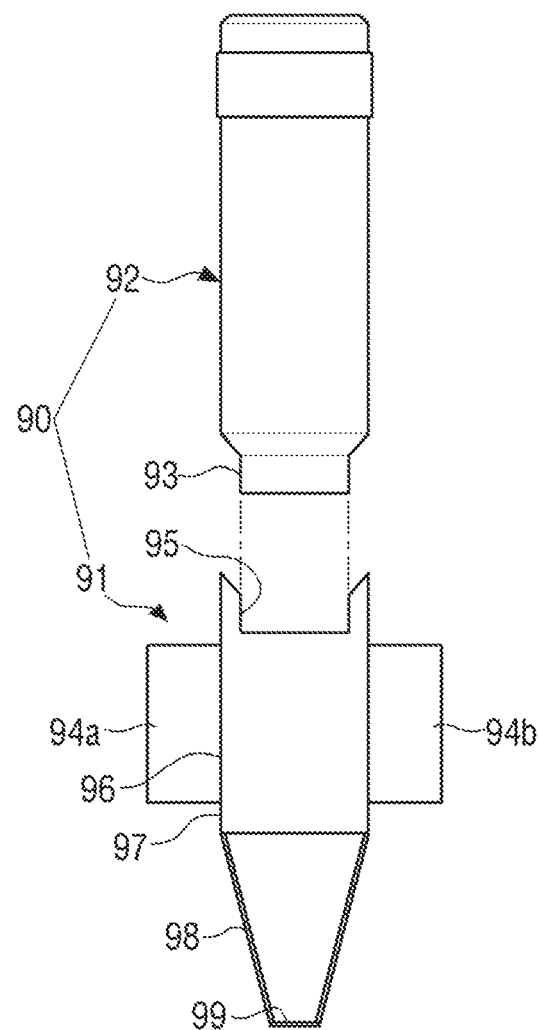
FIGS. 9A, 9B, and 10 are views to illustrate a detachable handpiece which is attachable to and detachable from a laser irradiation device using light according to an exemplary embodiment of the present disclosure.
Figure 9B:
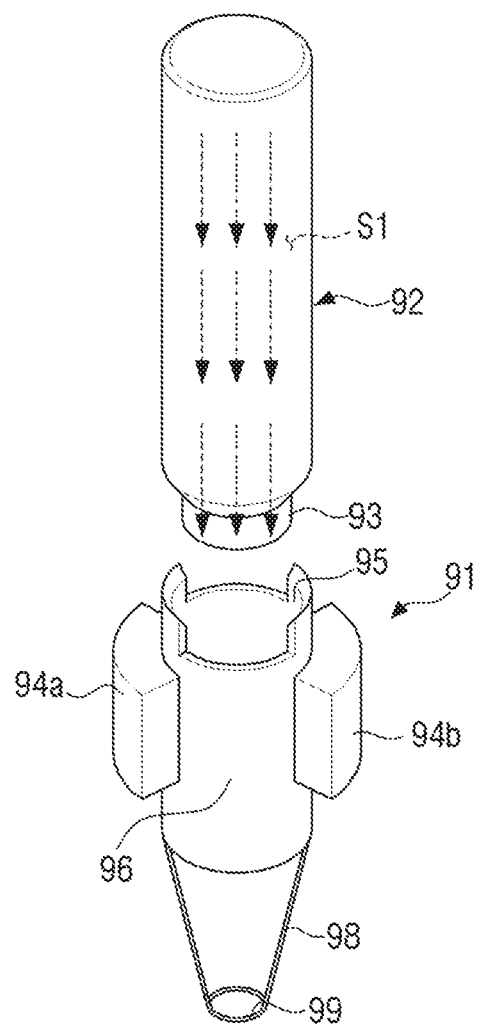
Figure 10:
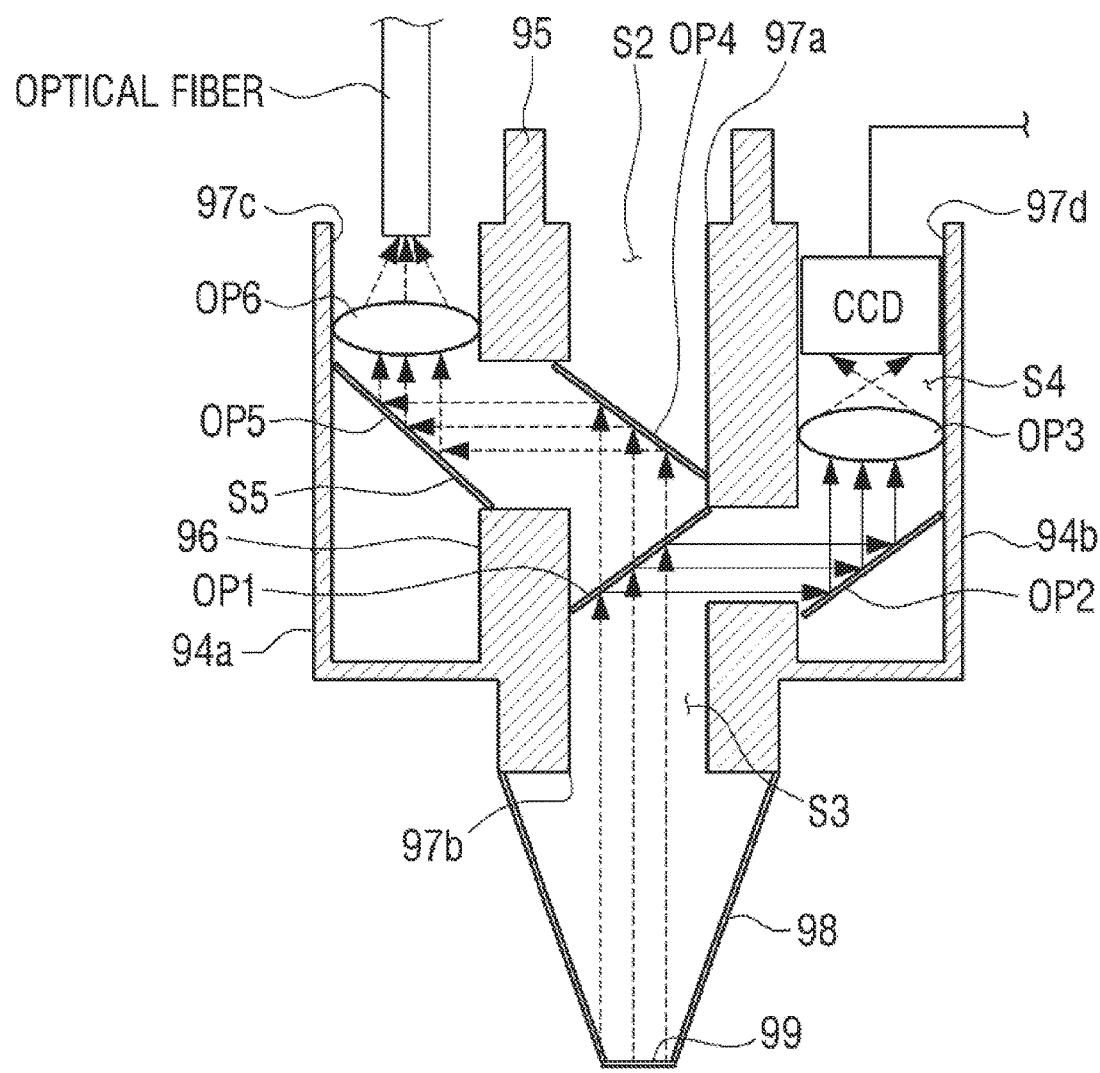

FIGS. 9 and 10 are views to illustrate a detachable handpiece which is attachable to or detachable from a laser irradiation device using light according to an exemplary embodiment of the present disclosure.

Referring to FIGS. 9 and 10, the detachable handpiece 91 which is attachable to or detachable from the laser irradiation device using the light according to an exemplary embodiment (hereinafter, referred to as a "detachable handpiece") is detachably connected with a handpiece 92 provided in the laser irradiation device. Herein, the laser irradiation device is a device which projects a collimated beam onto body tissue and has its own hand piece 92.

The detachable handpiece 91 according to an exemplary embodiment of the present disclosure is detachably connected with the handpiece 92 provided in the laser irradiation device.

The detachable handpiece 91 according to an exemplary embodiment is connected with the handpiece 92 provided in the laser irradiation device to form a handpiece 90 in the form of one piece. The handpiece 90 in the form of one piece may provide convenience to the user.

According to an exemplary embodiment, the handpiece 90 in the form of one piece, which is formed by connecting the detachable handpiece 91 according to an exemplary embodiment and the handpiece 92 provided in the laser irradiation device, may be substituted for the handpiece 3, the first light collection unit 20, and the second light collection unit 50 explained above with reference to FIG. 1. As will be explained below, an optical fiber of the handpiece 90 implemented in the form of one piece is connected to the spectrometer 61 of FIG. 1, and a CCD of the handpiece 90 implemented in the form of one piece corresponds to the CCD 30 of FIG. 1. The light provided from the laser main body 1 enters the handpiece 90 implemented in the form of one piece.

According to an exemplary embodiment, the handpiece 90 in the form of one piece, which is formed by connecting the detachable handpiece 91 according to an exemplary embodiment and the handpiece 92 provided in the laser irradiation device, may be substituted for the handpiece 3 and the complex light collection unit 70 explained above with reference to FIG. 4, 7, or 8. As will be explained below, the optical fiber of the handpiece 90 implemented in the form of one piece is connected to the spectrometer 61 of FIG. 1, and the CCD of the handpiece 90 implemented in the form of one piece corresponds to the CCD 30 of FIG. 1. The light provided from the laser main body 1 enters the handpiece 90 implemented in the form of one piece.

The detachable handpiece 91 according to an exemplary embodiment of the present disclosure includes a body part 96 which is formed in a cylindrical shape and includes spaces S2, S3, S4, and S5 formed therein to allow light to travel, a CCD which is disposed in the body part 96 to generate a digital image, and a light collection unit which is disposed in the body part 96 to split the generated light entering the body part 96 and emit the light to the spectrometer and the CCD.

Herein, the light traveling to the body part 96 may be a collimated beam which is provided from the laser irradiation device and light which is generated from the body tissue.

In this embodiment, the body part 96 includes a connection part 95, a laser inlet part 97*a* to receive light which is provided through the handpiece 92 provided in the laser irradiation device, a laser emission part 97*b* to emit the laser entering through the laser inlet part 97*a* to the body tissue, a generated light outlet part 97*c* to output the generated light to the outside, and an image outlet part 97*d* to output a digital image converted from the generated light.

Herein, the laser inlet part 97*a* and the laser emission part 97*b* have width and shape to allow the collimated beam to pass therethrough, and are aligned with each other so as to allow the collimated beam to pass therethrough.

The generated light outlet part 97*c* is connected with an optical fiber to provide the generated light to the optical fiber. An optical device OP6 provides the generated light to the optical fiber connected to the generated light outlet part 97*c*.

The image outlet part 97*d* has an electric wire disposed therein to be connected with the CCD. The digital image generated by the CCD is outputted to an external device (for example, the image data comparison unit) through the electric wire.

The body part 96 is formed in a cylindrical shape and has spaces formed therein to allow light to travel, and has the connection part 95 formed at one end of the cylindrical shape and the laser emission part 97b formed at the other end of the cylindrical shape.

The connection part 95 may be detachably connected with a connection part 93 of the handpiece 92 of the laser irradiation device. For example, screw structures may be formed on the connection part 93 and the connection part 95 to screw each other.

The laser emission part 97b is configured to receive the light generated from the body tissue, and also is configured to project a collimated beam provided from the laser irradiation device onto the body tissue. That is, the collimated beam provided from the laser irradiation device is outputted through the laser emission part 97b, and the light generated from the body tissue enters the body part 96 through the laser emission part 97b.

In this embodiment, the terms "laser emission part" and "generated light entering part" will be interchangeably used for reference numeral "97b". This is because the light generated from the body tissue may enter a part which is given reference numeral 97b, and the collimated beam provided from the laser irradiation device is emitted to the body tissue through the part which is given reference numeral 97b.

In this embodiment, the laser emission part and the generated light entering part are configured to be disposed at the same location. However, this is merely an example, and it will be understood by a person skilled in the art that the laser emission part and the generated light entering part may be disposed at different locations.

Optical devices OP1, OP2, OP3, OP4, OP5, and OP6 disposed in the body part 96 include a first optical module which splits at least part of the generated light entering through the generated light entering part 97b into a first direction and a second direction, and transmits the light; a second optical module which provides the light transmitted in the first direction to the optical fiber connected with the spectrometer; and a third optical module which provides the light transmitted in the second direction to the CCD.

In this embodiment, the first optical module may include two optical devices OP1 and OP4. From among these, the optical device OP1 splits the generated light entering through the generated light entering part 97b into the first direction and the second direction, and transmits the light, and the optical device OP4 provides the light transmitted in the first direction to the second optical module.

In this embodiment, the second optical module may include two optical devices OP5 and OP6. From among these, the optical device OP5 may provide the light provided from the optical device OP4 to the optical device OP6, and the optical device OP6 may provide the light provided from the optical device OP5 to the optical fiber connected with the spectrometer (not shown).

In this embodiment, the third optical module may include two optical devices OP2 and OP3. From among these, the optical device OP2 may provide the light provided from the optical device OP1 to the optical device OP3, and the optical device OP3 may provide the light provided from the optical device OP2 to the CCD.

In this embodiment, the body part 96 includes a first part, a second part, a third part, and a fourth part. Each of these parts provides a path to allow the light to travel therethrough.

The optical devices OP5 and OP6 may be disposed in the first part 94a, the optical devices OP2 and OP3 may be disposed in the second part 94b, and the optical devices OP1 and OP4 may be disposed in the third part. In addition, the third part is formed in a cylindrical shape to receive the collimated beam provided from the laser irradiation device and transmit the collimated beam to the body tissue as it is. The connection part 95 and the laser inlet part 97a are formed at one end of the third part, and the laser emission part 97b is formed at the other end of the third part.

The fourth part is provided as a guide part. Herein, the guide part may be connected with the laser emission part 97b of the third part and may include a ring 99 and a support part 98. The guide part serves to guide the collimated beam outputted through the laser emission part 97b to be projected onto a portion desired by the user. For example, the guide part is configured to allow the collimated beam outputted through the laser emission part 97b to pass through the center of the ring 99. Therefore, the user places the center of the ring 99 on the portion desired by the user and lets the collimated beam be transmitted.

In this embodiment, the collimated beam is provided from the laser irradiation device to the laser inlet part 97a, and is projected to the outside through the inside of the first part and the laser emission part 97b.

In this embodiment, the third part is disposed in the center of the body part 96, and the first part 94a and the second part 94b are disposed to enclose the third part. For example, the first part 94a and the second part 94b may be disposed to face each other.

The collimated beam provided from the laser irradiation device travels along the center axis of the third part. The guide part may be aligned to allow the collimated beam to be projected onto the body tissue through the center of the ring 99 of the guide part.

In the embodiments described with reference to FIGS. 9 and 10, the optical devices OP1 and OP4 may be configured not to influence the collimated beam projected onto the body tissue from each of the medical treatment devices.

While exemplary embodiments have been particularly shown and described above, it will be understood by those of ordinary skill in the art that various changes in form and details may be made therein without departing from the spirit and scope of the present invention as defined by the following claims.

What is claimed is:

1. A disease diagnosis apparatus for collecting light which is generated when light is projected onto body tissue and diagnosing a disease, the apparatus comprising:
   a first light collection unit configured to collect a part of the generated light;
   a second light collection unit configured to collect a part of the generated light;
   a spectrometer configured to analyze a spectrum of the light which is collected by the second light collection unit;
   a spectrum data comparison unit configured to compare the spectrum analyzed by the spectrometer and reference spectrum data;
   a CCD configured to convert the light collected by the first light collection unit into a digital image;
   an image data comparison unit configured to compare the digital image converted by the CCD and a reference image;
   a disease diagnosis unit configured to determine whether there is a disease in the body tissue based on at least one of a comparison result of the spectrum data comparison unit and a comparison result of the image data comparison unit, and a SELIES (Surface Enhanced Laser Induced Emission Spectroscopy) film,
wherein the SELIES (Surface Enhanced Laser Induced Emission Spectroscopy) film has a function of enhancing a signal intensity of the generated light,
wherein the SELIES (Surface Enhanced Laser Induced Emission Spectroscopy) film is disposed on the body tissue, and
wherein the light projected onto the body tissue is a collimated light.

2. The apparatus of claim 1, further comprising a related data generation unit configured to generate related data which defines a relationship between the digital image converted by the CCD and the spectrum data analyzed by the spectrometer.

3. The apparatus of claim 1, wherein the SELIES (Surface Enhanced Laser Induced Emission Spectroscopy) film comprises a substrate and a layer for enhancing the signal intensity of the generated light,
wherein the layer is temporarily or fixedly formed on the surface of the substrate.

4. The apparatus of claim 1, wherein the second light collection unit comprises an optical module configured to provide a part of the generated light collected by the second light collection unit to an optical fiber connected to the spectrometer.

5. The apparatus of claim 1, wherein the first light collection unit comprises an optical module configured to provide a part of the generated light collected by the first light collection unit to the CCD.

6. A disease diagnosis apparatus for collecting light which is generated when light is projected onto body tissue and diagnosing a disease, the apparatus comprising:
a complex light collection unit configured to collect at least part of the generated light;
a spectrometer configured to analyze a spectrum of a part of the light which is collected by the complex light collection unit;
a spectrum data comparison unit configured compare the spectrum analyzed by the spectrometer and reference spectrum data;
a CCD configured to convert a part of the light collected by the complex light collection unit into a digital image;
an image data comparison unit configured to compare the digital image converted by the CCD and a reference image;
a disease diagnosis unit configured to determine whether there is a disease in the body tissue based on at least one of a comparison result of the spectrum data comparison unit and a comparison result of the image data comparison unit, and
a SELIES (Surface Enhanced Laser Induced Emission Spectroscopy) film,
wherein the SELIES (Surface Enhanced Laser Induced Emission Spectroscopy) film has a function of enhancing a signal intensity of the generated light,
wherein the SELIES (Surface Enhanced Laser Induced Emission Spectroscopy) film is disposed on the body tissue, and
wherein the light projected onto the body tissue is a collimated beam.

7. The apparatus of claim 6, further comprising a related data generation unit configured to generate related data which defines a relationship between the digital image converted by the CCD and the spectrum data analyzed by the spectrometer.

8. The apparatus of claim 6, wherein the SELIES (Surface Enhanced Laser Induced Emission Spectroscopy) film comprises a substrate and a layer for enhancing the signal intensity of the generated light,
wherein the layer is temporarily or fixedly formed on the surface of the substrate.

9. The apparatus of claim 6, wherein the complex light collection unit is configured to split the collected light into the spectrometer and the CCD.

10. The apparatus of claim 9, wherein the complex light collection unit comprises a first optical module configured to split a part of the collected light into a first direction and a second direction, and transmit the light, a second optical module configured to receive at least part of the light transmitted from the first optical module in the first direction; and a third optical module configured to receive at least part of the light transmitted from the first optical module in the second direction,
wherein the second optical module is configured to provide the at least part of the light received from the first optical module to an optical fiber connected with spectrometer, and
wherein the third optical module is configured to provide the at least part of the light provided from the first optical module to the CCD.

11. The apparatus of claim 10, wherein the third optical module comprises two optical devices,
wherein a first optical device of the two optical devices is configured to receive at least part of the light which is generated when the light is projected onto the body tissue, and provide the light to a second optical device of the two optical devices,
wherein the second optical device is configured to split the light received from the first optical device into the first direction and the second direction,
wherein the second optical module is configured to receive at least part of the light split into the first direction, and the third optical module is configured to receive at least part of the light split in the second direction.

12. The apparatus of claim 10, wherein the first optical module comprises two optical devices,
wherein a first optical device of the two optical devices is configured to receive at least part of the light which is generated when the light is projected onto the body tissue, and split the light into the first direction and the second direction,
wherein a second optical device of the two optical devices is configured to provide at least part of the light split into the first direction to the second optical module, and the third optical module is configured to receive at least part of the light split into the second direction.

13. A detachable handpiece for disease diagnosis, which is attachable to or detachable from a laser irradiation device which is able to perform an operation for medical or beauty care using light, the detachable handpiece comprising:
a body part having a cylindrical shape, the body part comprising:
a path formed therein to allow light to travel,
a generated light entering part configured to receive light which is generated when light is projected onto body tissue by the laser irradiation device, and
a connection part detachably connected with the laser irradiation device;
a CCD disposed in the body part to generate a digital image; and a light collection unit configured to split the generated light entering through the generated light entering part into a spectrometer and the CCD, wherein the CCD is configured to generate the digital image corresponding to the light provided from the light collection unit, and wherein the laser projected onto the body tissue by the laser irradiation device is a collimated beam, wherein the light collection unit comprises:

an optical module configured to split at least part of the generated light entering through the generated light entering part into a first direction and a second direction, and transmit the light;

an optical module configured to provide the light transmitted in the first direction to an optical fiber connected to the spectrometer; and an optical module configured to provide the light transmitted in the second direction to the CCD, and a SELIES (Surface Enhanced Laser Induced Emission Spectroscopy) film, wherein the SELIES (Surface Enhanced Laser Induced Emission Spectroscopy) film has a function of enhancing a signal intensity of the generated light, and wherein the SELIES (Surface Enhanced Laser Induced Emission Spectroscopy) film is disposed on the body tissue.

14. The detachable handpiece of claim 13, wherein the body part comprises a first part having a space to allow light to travel therein, a second part having a space to allow light to travel therein, and a third part having a space to allow light to travel therein, wherein at least part of the optical module for providing the light transmitted in the first direction to the optical fiber is disposed in the first part, wherein the optical module for providing the light transmitted in the second direction to the CCD is disposed in the second part, wherein the optical module for splitting at least part of the generated light entering through the generated light entering part into the first direction and the second direction and transmitting the light is disposed in the third part, wherein the light projected onto the body tissue enters through one end of the third part, travels through the inner space formed in the third part, and then is projected through the generated light entering part formed at the other end of the third part.

15. The detachable handpiece of claim 14, wherein the third part is disposed in the center of the body part, and the first part and the second part are disposed to enclose the third part.

16. The detachable handpiece of claim 15, wherein the first part and the second part are disposed to face each other.

17. The detachable handpiece of claim 14, wherein the optical module for providing the light transmitted in the first direction to the optical fiber comprises:

one or more optical devices configured to change a direction of light, and an optical device configured to place a focal point of light the direction of which has been changed by the one or more optical devices on the optical fiber.

18. The detachable handpiece of claim 13, wherein the generated light entering through the generated light entering part is a collimated beam.

* * * * *